(12) United States Patent
Suovaniemi et al.

(10) Patent No.: US 7,563,409 B2
(45) Date of Patent: Jul. 21, 2009

(54) METHOD OF ATTACHING A PIPETTE TIP AND AN APPARATUS FOR SUCH METHOD

(75) Inventors: Osmo Suovaniemi, Helsinki (FI); Pertti Ekholm, Helsinki (FI)

(73) Assignee: Biohit Oyj, Helsinki (FI)

( * ) Notice: Subject to any disclaimer, the term of this patent is extended or adjusted under 35 U.S.C. 154(b) by 743 days.

(21) Appl. No.: 10/963,731

(22) Filed: Oct. 14, 2004

(65) Prior Publication Data
US 2005/0125163 A1 Jun. 9, 2005

(30) Foreign Application Priority Data
Oct. 17, 2003 (FI) .................................. 20031521

(51) Int. Cl.
*B01L 3/02* (2006.01)
(52) U.S. Cl. .................. 422/100; 422/99; 222/287; 222/288; 222/326; 73/864.18
(58) Field of Classification Search ........... 422/99–100; 222/287–288, 326; 73/864.18
See application file for complete search history.

(56) References Cited

U.S. PATENT DOCUMENTS

| 4,529,401 A |   | 7/1985  | Leslie et al.    |          |
|-------------|---|---------|------------------|----------|
| 4,671,123 A | * | 6/1987  | Magnussen et al. | 73/864.16|
| 4,785,677 A |   | 11/1988 | Higo             |          |
| 5,620,661 A |   | 4/1997  | Schurbrock       |          |
| 2001/0019701 A1 | | 9/2001 | Braun et al.    |          |

FOREIGN PATENT DOCUMENTS

FI          109337 B        7/2002

* cited by examiner

*Primary Examiner*—Jill Warden
*Assistant Examiner*—Jyoti Nagpaul
(74) *Attorney, Agent, or Firm*—Birch, Stewart, Kolasch & Birch, LLP

(57) ABSTRACT

The object of this invention is a method for attaching a pipette tip and an apparatus for such method. The method comprises the following steps: opening the interlocking which attaches the replaceable part with the help of electronically controlled interlocking mechanism for detaching or receiving the replaceable part; saving the information of the opening of the interlocking mechanism to the control electronics of the pipette; closing the interlocking which attaches the replaceable part with the help of the electronically controlled interlocking mechanism for attaching the replaceable part; saving the information of the closing of the interlocking mechanism to the control electronics of the pipette; providing the dispensing parameters and/or type and/or size of the replaceable part with the help of a keyboard to the control electronics to ensure the attachment of a desired replaceable part and to achieve pipetting readiness. The object of this invention is thus also to present a pipetting apparatus where the setting mechanism of the replaceable part is so arranged that it prevents accidentally performed setting mistakes but does not require using of a special tip.

9 Claims, 3 Drawing Sheets

METHOD OF ATTACHING A PIPETTE TIP AND AN APPARATUS FOR SUCH METHOD

This Non-provisional application claims priority under 35 U.S.C. § 119(a) on Patent Application No(s). 20031521 filed in Finland on Oct. 17, 2003, the entire contents of which are hereby incorporated by reference.

The object of this invention is a method according to claim 1 for attaching a pipette tip, and an apparatus for such method.

Such liquid handling systems are previously known where functional parameters of an attached replaceable part which receives the liquid to be portioned are input through a keyboard for programming a device. Such an infusion pump is disclosed for example in the publication U.S. Pat. No. 4,529,401. However this publication does not disclose removing of the replaceable part with an electronic or electronically controlled tip lock.

Manual liquid portioning in laboratories is usually performed with so called air displacement pipettes which are easy and economical to use. However there are situations when the efficiency of an air displacement pipette is not enough and then the user chooses a pipette where a disposable plunger-cylinder combination is attached. Typically then is used liquids which have a high viscosity or which evaporate easily. Pipettes with disposable plunger-cylinder combinations are especially suitable in so called series portioning which enables step by step removing of the liquid from the syringe.

When using such replaceable plunger-cylinder combinations used in mechanical pipettes the user places the replaceable part to its position, sets the parameter which usually effects to the portioning strike and then views a separate chart which volume the strike in question gives with each tip type. Cumbersomeness of using such plunger-cylinder combinations and separate charts extremely well emphasize the advantages which result from the invention at hand, such as easy usage and accurate portioning parameters.

Later for the previously mentioned situations has been developed pipetting systems where the attached replaceable part is identified. In known pipetting systems, where there is arranged means for identifying different tip types, such as for example disclosed in the patent publication FI109337, also the replaceable part must be equipped with identifying means, so when choosing the replaceable parts, i.e. tips, the user of the pipetting system must use special tips.

In conventional pipettes the volumes are adjusted with settings of the pipette and the tips of different sizes differ from each other with cones of different sizes. When using plunger-cylinder combinations, all different volumes have the attachment means of the same size and thus the risk for attaching a wrong plunger-cylinder combination is very high.

One object of this invention is thus also to present a pipetting apparatus where the setting mechanism of a replaceable part is so arranged that it prevents accidentally perfomed setting mistakes but does not require using of the special tips.

This object can be acquired by using an electronic or electronically controlled liquid hadling device which has en electronically controlled tip lock to perform the method of this invention. Preferably the basic construction of the liquid handling device can be for example of the same type as pipettes with an electronic tip remover in Biohit's eLINE-series.

Figure 3:
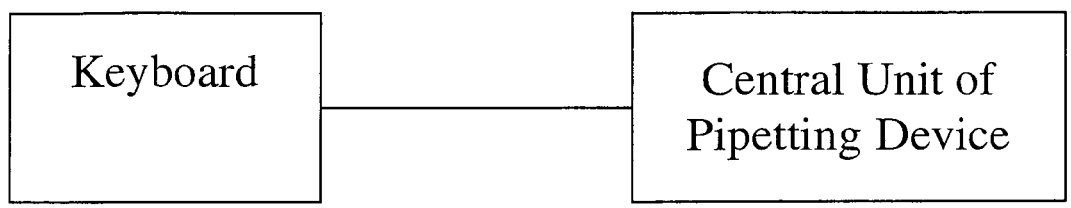
FIG. 3 schematically shows an example of a keyboard with a central unit of a pipetting device of the present invention.

More precisely in a method according to the invention the replaceable part is removed from the pipette with an electronically controlled interlocking mechanism in the pipette, which information of the removal is supplied to the control electronics of the pipette, which control electronics after this prevents performing of pipetting actions until it has received information about attachment of a new replaceable part and for example the portioning parameters of the replaceable part, type and size of the replaceable part, which are input to a central unit of the pipetting device through a keyboard which appertains to the pipetting device (see FIG. 3).

In this method the attachment of the replaceable part to be attached to the pipetting device is ensured with the following steps: interlocking which attaches the replaceable part is opened with an electronically controlled interlocking mechanism for detaching the replaceable part or for receiving it, whereupon the information about the opening of the interlocking mechanism is saved, preferably automatically, to the control electronics of the pipette. After this the interlocking which attaches the replaceable part is closed with the electronically controlled interlocking mechanism for attaching the replaceable part, where after the attachment the information about the closing of the interlocking mechanism is saved, preferably automatically, to the control electronics of the pipette, where after the save the pipetting device will not function before the information about the replaceable part is input through a keyboard to the control electronics of the pipette. After this the portioning parameters of the replaceable part are input through the keyboard to the control electronics of the pipetting device to ensure the attachment of a sought-after replaceable part and to accomplish the pipetting readiness.

One preferred embodiment of the invention is a method where the replaceable part is a plunger-cylinder unit, whose plunger in a replaceable part placed in the pipetting device is moved with a plunger adjustment means of the pipetting device in relation to the cylinder during a pipetting movement to take and remove the liquid to be pipetted, when different replaceable parts are arrangeable to the pipetting device, when still for all the different types the same relative position of the plunger and the cylinder is arranged.

Preferably the method according to the invention is performed with a device which is an electronically controlled pipette and which comprises a body which comprises an end part and where the detachable replaceable part is received. In addition to this the apparatus comprises an electronic control means which controls the functions of the pipette, and an executing keyboard and a plunger movable in the longitudinal direction of the body to portion the liquid to be pipetted. In addition the pipette further comprises electronically controlled interlocking means with which the detachable part is interlocked to its position and detached, and there is means for inputting the status of the interlocking means to the electronic control means, preferably such means is a program. With a keyboard of the device the portioning parameters of the replaceable part and/or type and/or size are input to the electronic control means to ensure the attachment of the sought-after replaceable part and to accomplish the pipetting readiness.

Also a preferred embodiment is an apparatus which is a an electronically controlled pipette which comprises a body which comprises an end part where the detachable replaceable part is received; an electronic control means which controls the functions of the pipette; an executing keyboard with which the portioning parameters of the replaceable part are input to the electronic control means; a plunger which is movable in the longitudinal direction of the pipette to portion the liquid to be pipetted; an electronically controlled interlocking means which move in the cross direction of the pipette body with which the detachable replaceable part is locked or removed; a directing means to direct the movement of the interlocking means to the direction which deviates from the longitudinal direction; and the movement of the plunger is continued so that the continued longitudinal movement of the plunger is turned to deviate from the longitudinal movement with the directing means which direct the movement of the interlocking means, then the replaceable part is preferably removed in the axial direction.

According to the invention also a pipetting system can be formed which comprises an electronic pipetting device or an electronically controlled pipetting device, to which pipetting device there is detachably attached a replaceable part which receives the liquid to be pipetted, which replaceable part is formed as a plunger-cylinder unit, whose plunger in the replaceable part inserted in the pipetting device is moved with a plunger adjusting means of the pipetting device in relation to the cylinder during pipetting movement for receiving a sample or removing it, then to the pipetting device there is arranged different, different type of replaceable parts when still for all the different types there is arranged one and the same relative position of the plunger and the cylinder.

Figure 1:
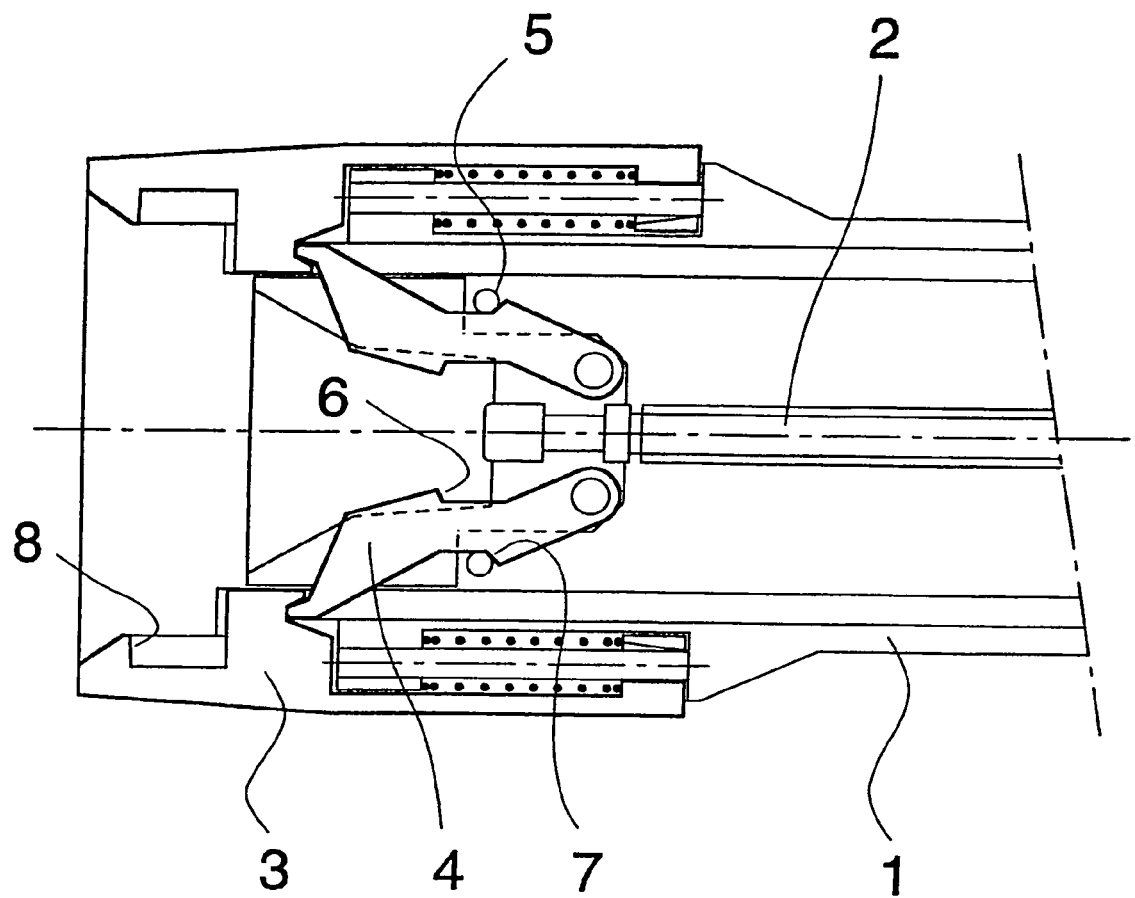
FIG. 1 shows an example of an interlocking arrangement used in a pipetting system of the present invention.

Thus preferably the method according to the invention can be performed with a device which enables using of the pipette with only one hand in all situations. The interlocking arrangement used in such a pipetting system is presented in FIG. 1, which is referred to in the following example.

Example: Pipetting system which is a pipetting device, such as an electronic pipette, equipped with an electronic control, which comprises a body part (1), and to which pipetting device is detachably connected a replaceable part, which receives the liquid to be pipetted, which replaceable part is formed as a plunger-cylinder unit, which plunger of the replaceable part is moved with a plunger (2) of the pipetting device in relation to the cylinder during a pipetting movement to receive and remove liquid, when it is possible to equip the pipetting device with different, different type of replaceable parts, when still for all types it is arranged one and same relative position of the plunger and the cylinder.

The electronic pipette can be a hand-held, battery using, microprocessor controlled pipette, where there is a body part, which encloses a motor with power supply devices, a control means for controlling the motor and which comprises a means to control the pipette functions, a display, an end part, where in a cylinder space of the cylinder there is a back-and-forth moving plunger for changing the volume of the cylinder space and a means for changing the rotating movement of the motor to a substantially longitudinal movement of a plunger in a longitudinal direction of the pipette body. Means which control the functions of the pipette are preferably formed from a microprocessor, which comprises in addition to a central unit at least a memory means for constant saving of information and/or programs and for temporary saving of information and/or programs, and a means for connecting the microprocessor to the means controlling the display, to the buttons and/or switches controlling the functions, to the sensors for identifying the status of the functioning means and to means for carrying the control signals from the microprocessor to the control means of the motor. The information and programs saved in the memory means can be saved in the manufacturing phase of the pipette or the user can save them while using the pipette.

According to this example the replaceable part can be placed so that it goes at least partly inside the pipetting device. There is a receiving space in the pipette for the replaceable part and a receiving piece, where there is a plunger receiving space for a syringe plunger; in addition there is a means for recovering attachment of the connection part and the syringe plunger so that they can be attached to their receiving openings. Also plunger adjustment means is arranged in the pipette to move the receiving piece in the pipette body; and an attaching part and the syringe plunger are in an axial direction moved through an opening in their receiving opening's axial direction to their attachment positions. According to the invention the pipette also comprises gripping means (3) which are adjustable in a radial direction for attaching a syringe, and the pipette further comprises: an operating arm (4) which is turnably beared to the receiving piece, which is connected to the gripping means, for moving the gripping means in the radial direction; a support point (5), which drives the movement of the operating arm; the operating arm comprises a first shoulder (6), which connects the syringe plunger to its attachment position and a second shoulder (7), which is connected with a support point in a pipette body, with the help of the second shoulder and support point the axial movement of the receiving piece while continuing forced by the plunger of the pipette outside the normal dispensing work area for removing and/or receiving the syringe and the syringe plunger is possible to direct also in the radial direction, when while the gripping means move in the radial direction the syringe releases from the attachment notch (8) and the syringe plunger from the shoulder (6). The pipetting device also comprises a central unit which controls the functions, which controls the functioning of the pipette and interlocking mechanism of the replaceable part, and to where the dispensing parameters and/or type and/or size of the replaceable part are transmitted through a keyboard.

Figure 2:
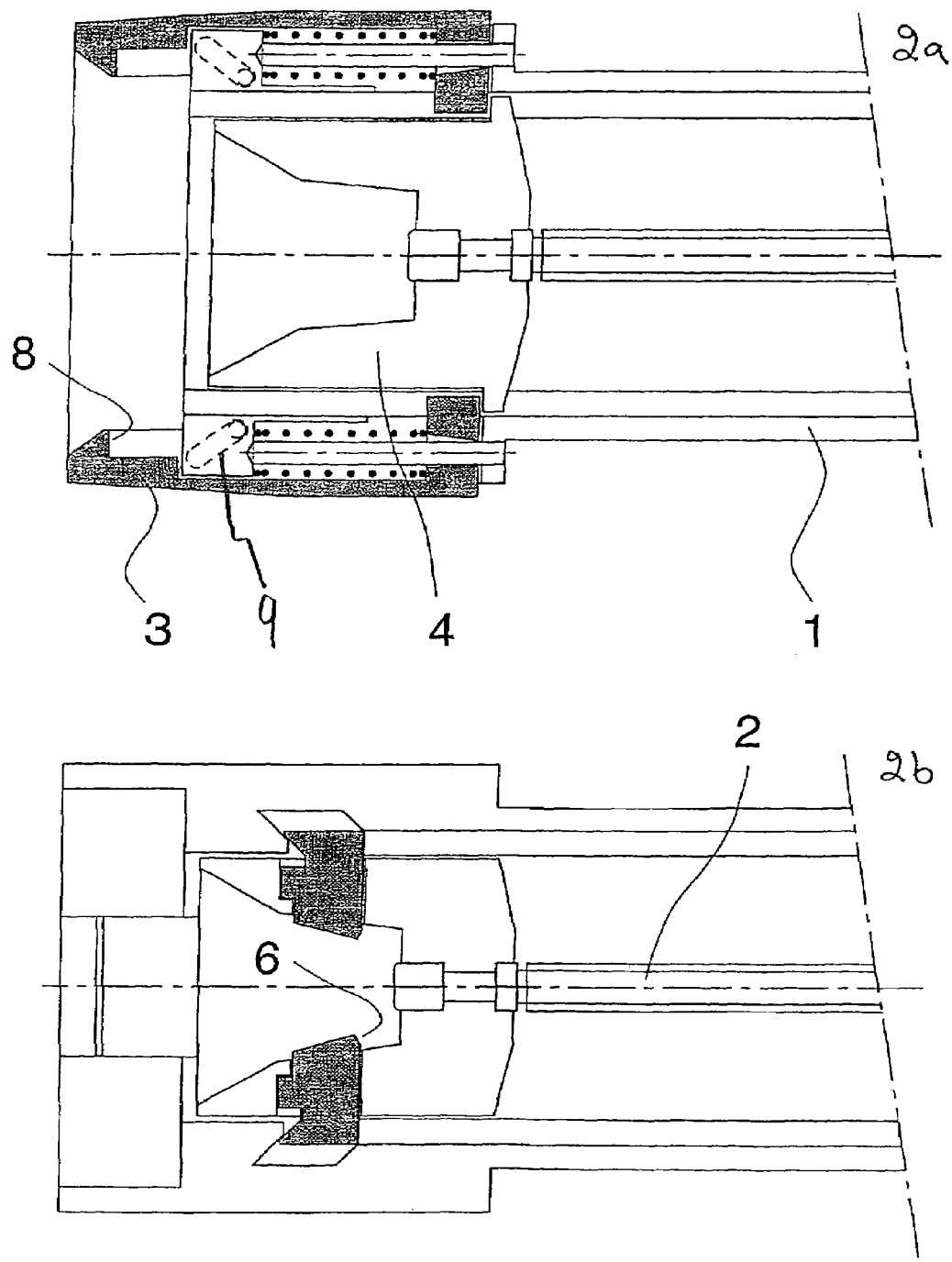
FIG. 2*a* shows an example of an attaching mechanism of a syringe of a pipetting system of the present invention.
FIG. 2*b* shows an example of an attaching mechanism of a syringe plunger of the present invention.

FIG. 2 depicts an alternative mechanical implementation for the tip lock, which figure is intended for pointing out how the method according to the invention can be utilized regardless of the function mechanism of the tip lock. Picture 2a in FIG. 2 depicts the attaching mechanism of the syringe of the pipetting system according to the example. The operating arm 4 avoids the longitudinal movement while penetrating downwards consequently to the continued movement of the plunger of the pipette, which with driving means (i.e., directing means) (9) presented with dashed lines turns the movement of the interlocking means (i.e., electronically controlled interlocking means) (3) to the radial direction, then the attachment notch (8) unfastens from the syringe.

Picture 2b in FIG. 2 depicts an attaching mechanism of a syringe plunger, which is distinct from the attaching mechanism of the actual syringe. The continued movement of the plunger (2) of the pipette pushes with the help of the syringe plunger the longitudinal movement to the shoulder, which in this case is arranged to be bevel, when the longitudinal movement turns with the help of tracks to an axial movement of the interlocking means.

The invention claimed is:

1. A method for securing an attachment of and identifying a replaceable part which receives a liquid to be pipetted and which is attachable to a pipetting device, comprising the steps of:
opening an interlocking which attaches the replaceable part with the help of an electronically controlled interlocking mechanism for detaching or receiving the replaceable part;
saving information of opening of the interlocking mechanism to a control electronics of a pipette;

closing the interlocking which attaches the replaceable part with the help of an electronically controlled interlocking mechanism for attaching the replaceable part;

saving information of closing of the interlocking mechanism to the control electronics of the pipette; and providing dispensing parameters and/or type and/or size of the replaceable part with the help of a keyboard to the control electronics to ensure the attachment of a desired replaceable part and to achieve a pipetting readiness.

2. The method according to claim 1, wherein the replaceable part is a plunger-cylinder unit, whose plunger, when the replaceable part is attached to the pipetting device, is moved with the help of a plunger adjustment means in relation to the cylinder during the pipetting movement for receiving and removing liquid to be pipetted, whereat it is possible to arrange different types of replaceable parts to the pipette device, whereat still for all types it is arranged one and the same relative position of the plunger and the cylinder.

3. An electronically controlled pipette, which comprises:

a body, which comprises an end part, where a detachable replaceable part is receivable;

an electronic control means, which control the functioning of the pipette;

an executing keyboard;

a plunger movable in a longitudinal direction of the body for portioning liquid to be pipetted;

an electronically controlled interlocking means, with which the detachable replaceable part is interlockable to its position or detachable; and a means for carrying the status of the interlocking means to the electronic control means; wherein with the keyboard, the dispensing parameters and/or type and/or size of the replaceable part can be inputted to the electronic control means to ensure the attachment of a desired replaceable part and to achieve a pipetting readiness.

4. The electronically operated pipette according to claim 3, further comprising:

a directing means for directing the movement of the interlockable means to a direction that differs from the longitudinal direction, wherein the interlocking means is adjustable in crosswise direction of the body, with which the replaceable part is interlockable to its position or detachable, and the plunger is continuously movable so that the plunger is turnable to a direction different from the longitudinal direction with the directing means which directs the movement of the interlocking means.

5. The electronically operated pipette according to claim 3 or 4, wherein the replaceable part is a plunger-cylinder combination.

6. A pipetting system which comprises:

a syringe with an attaching part;

a syringe plunger; and a suction device, wherein in the suction device comprises:

a body, which comprises an end part, where a detachable or replaceable part is receivable;

an electronic control means, which control a function of the pipette;

an executing keyboard;

a plunger movable in a longitudinal direction of the body for portioning liquid to be pipetted;

an interlocking means which is movable in crosswise direction of the body, with which the detachable or replaceable part is interlockable to its position or detachable; and a directing means for directing the movement of the interlockable means to a direction that differs from the longitudinal direction, wherein the plunger is continuously movable so that the plunger is turnable to a direction different from the longitudinal direction with directing means which direct the movement of the interlocking means, and with the keyboard the dispensing parameters can be inputted to the electronic control means.

7. The pipetting system according to claim 6, wherein the suction device further comprises:

a receiving space in the body for the attachment part;

a receiving part, where the receiving space of the plunger for the syringe plunger;

an attachment means for detachably attaching the attachment part and/or the syringe plunger to their receiving openings; and an adjusting means of the plunger for moving the receiving part inside the pipette body, wherein the receiving part and the syringe plunger are movable through openings in an axial direction of their receiving openings to their receiving positions.

8. The pipetting system according to claim 7, further comprising:

an operating arm turnably disposed to the receiving piece which is connected to a gripping means, to move a gripping means in a radial direction; and a support point which directs the movement of the operating arm wherein the operating arm comprises a first shoulder which attaches the syringe plunger to its attachment position and a second shoulder which is connected to the support point in the pipette body, and with the help of the second shoulder and the support point, the receiving piece for detaching and/or attaching the syringe and the syringe plunger is directable in the axial and radial directions.

9. The pipetting system according to claim 6, wherein an attachment means is arranged for the attaching part and the syringe plunger, respectively, and each of the attachment means has a distinct directing means, the distinct directing means being movable in the radial direction with the help of the attachment means.

* * * * *